United States Patent [19]

Cooper

[11] 4,328,806
[45] May 11, 1982

[54] CATHETER WITH TRANS-LUMINAL GAS PATHWAY

[75] Inventor: Robert P. Cooper, Yorba Linda, Calif.

[73] Assignee: American Hospital Supply Corporation, Evanston, Ill.

[21] Appl. No.: 160,750

[22] Filed: Jun. 18, 1980

[51] Int. Cl.³ .......................................... A61M 25/00
[52] U.S. Cl. ................................ 128/349 B; 128/642; 128/786
[58] Field of Search ................... 128/349 B, 672, 673, 128/675, 692, 713, 768, 786; 156/48; 174/20, 22 R, 23 R, 256, 266

[56] References Cited

U.S. PATENT DOCUMENTS

| | | | |
|---|---|---|---|
| 2,052,422 | 8/1936 | Rottsieper | 174/23 R |
| 3,448,739 | 6/1969 | Stark et al. | 128/673 |
| 3,955,623 | 12/1976 | Blake et al. | 128/642 |
| 4,147,169 | 4/1979 | Taylor | 128/349 B |
| 4,216,349 | 8/1980 | Wium | 174/23 R |
| 4,222,384 | 9/1980 | Birtwell | 128/349 B |

*Primary Examiner*—William E. Kamm
*Attorney, Agent, or Firm*—Tilton, Fallon, Lungmus et al.

[57] ABSTRACT

A catheter having at least two separate lumens, one for conveying liquids to and from a port spaced substantially from the distal end of the catheter and the other for enclosing an electrical conductor which extends to a point distal to the port. The two lumens are separated by a longitudinal septum and combine to perform a third function—that of containing a gas required in connection with the operation of a pressure responsive element adjacent the catheter's distal end. The septum is provided with an aperture through which the gas chamber or pathway switches from one lumen to the other. A sealant plug located in the lumen for liquid flow prevents contact between such liquid and both the electrical conductor and the gas within the pathway. Methods for forming such a catheter are also disclosed.

16 Claims, 10 Drawing Figures

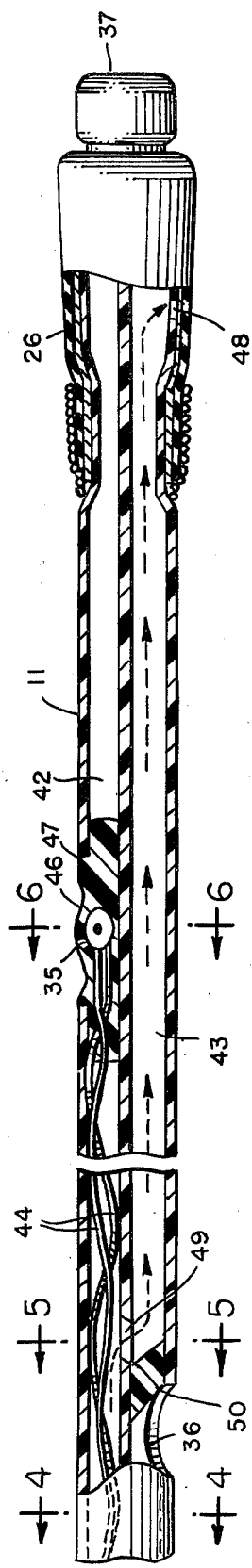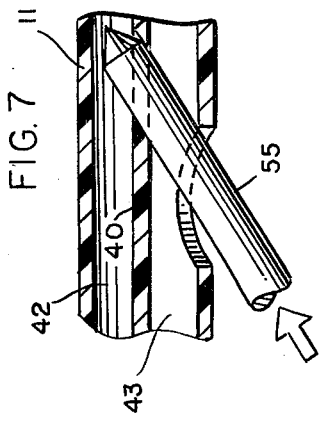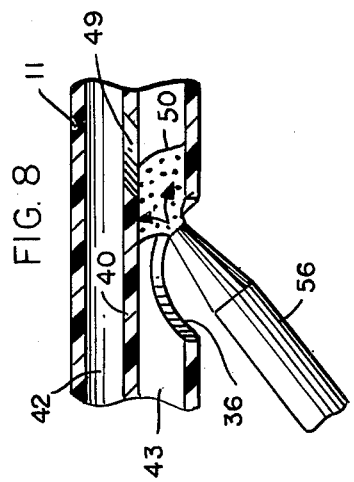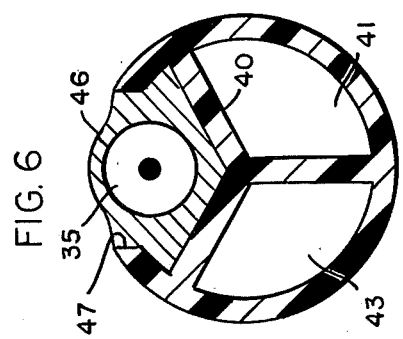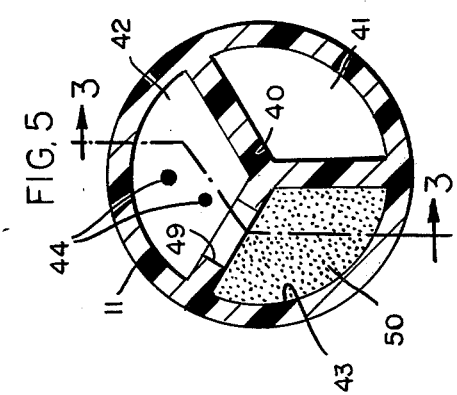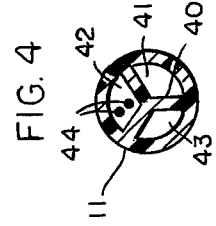

CATHETER WITH TRANS-LUMINAL GAS PATHWAY

BACKGROUND

U.S. Pat. No. 3,995,623 discloses a multi-lumen flow-directed catheter suitable for use in diagnosing cardiovascular and pulmonary diseases. When the catheter is used for thermodilution measurements, a bolus of cold liquid is injected into the right atrium or superior vena cava (through port 30) and the resultant change in blood temperature is detected by a thermistor (represented by numeral 35) in the pulmonary artery, such change in blood temperature being representative of cardiac output. Three lumens are required by the patented construction to achieve such operation, one lumen conducting gas for balloon inflation, another conveying liquid for the injection of the cold bolus (or for right atrium pressure monitoring, blood sampling, or infusion of therapeutic media) and a third carrying the thermistor leads. One or more additional lumens would be provided where further capabilities are desired; thus, the patent discloses a fourth lumen (C) which extends completely through the catheter body for use in measuring pulmonary arterial pressures when the catheter is in place and the balloon is deflated, or pulmonary capillary wedge pressures when the balloon is inflated.

While the multiple function capability is an important objective, especially for heart catheterization where it is desirable to obtain as much diagnostic information as possible in a single catheterization procedure, such an objective has been achieved in the past either by increasing the size (outside diameter) of such a catheter or by reducing the cross section of each lumen and, hence, lowering the performance characteristics of the catheter. Not only must the lumens be made smaller, if their number is to be increased without altering the catheter's outside dimensions, but the necessity of providing septa between the lumens requires a further reduction in lumen size. Even when the partitions or septa which define the multiple lumens are made as thin as possible, their thickness still substantially reduces the space available for the several lumens within a catheter of any given size. At the same time, the outside dimensions of such a catheter, which must be capable of passing through the vascular system without injury to the patient, must be kept as small as possible. A 4 French catheter (approximately 0.053 inch O.D.) would therefore generally be considered more desirable than a larger 6 French (0.078 inch O.D.) catheter in terms of ease of manipulation, and reduced risk of possible complications in use. Consequently, in order to achieve multiple functions in a cardiac catheter of optimum size, it has generally been considered necessary to compromise the performance capabilities of such a catheter.

Other U.S. Pat. Nos. disclosing multiple-lumen catheters are 3,746,003, 3,833,004, 3,710,781, 3,634,924, 3,152,592, 3,044,468, 3,050,066, and 2,845,930.

SUMMARY

This invention lies in part in the discovery that in the construction of a catheter having a proximal port for cold bolus introduction (or for blood sampling or pressure measurements) and a distal thermistor or other electrical element, the two lumens used for such purposes may also be adapted for joint use as a gas pathway or chamber, thereby eliminating a third separate lumen previously thought to be necessary for the latter purpose. Since the space which such a lumen would have occupied may be used to increase the cross sectional dimensions of the other lumens, and since the space which would have been occupied by a septum needed for the purpose of defining a separate gas-transmitting lumen also becomes available, the result is that a catheter made in accordance with this invention would have superior flow capacity and other performance characteristics when compared with a conventional catheter of similar outside dimensions. Viewed differently, the present invention makes it possible to reduce substantially the outside dimensions of a plural-lumen catheter without at the same time reducing its performance characteristics.

Such objectives have been achieved by eliminating the separate lumen which would contain gas required in connection with the operation of pressure responsive means adjacent the distal end of the catheter and by providing a gas pathway through portions of the other lumens in such a manner that the electrical leads remain isolated from possible liquid contact. In the disclosed embodiment, the gas pathway extends through the lumen containing the electrical leads from the proximal end of the catheter to an intermediate point, at which point the pathway extends through an aperture in the longitudinal septum separating the lead-containing lumen from a second lumen used for bolus injection and other diagnostic functions. The gas pathway then continues through the second lumen to a distal point where a balloon or other pressure responsive element is located. Liquid cannot enter either the distal portion of the second lumen or any portion of the first lumen because of a sealant plug in the second lumen adjacent to the port for bolus discharge. At the same time, the sealant plug is formed and/or located to maintain the distal portion of the second lumen in flow communication with the first lumen through the aperture in the longitudinal septum.

In practicing the method of the invention, a lateral port may first be formed in the outer wall of the catheter body at an intermediate point, the port being located so that it communicates only with the lumen of the catheter intended to convey liquid for bolus injection, blood sampling, or pressure measurements. A suitable tool may then be inserted through the port to form an aperture in the septum which separates the lumen for liquid flow from a parallel lumen intended to contain the electrical leads. In one form of the invention, the aperture is located just distal to the port, a procedure which may be readily accomplished by inserting the tool through the port at an angle so that the tip of the tool pierces the septum at a distally-offset point. In another embodiment of the invention, the aperture is positioned generally within the longitudinal limits of the port; that is, the aperture is in general radial alignment with the port. In either case, a sealant plug is then located within the second lumen (the liquid-transmitting lumen) in such a way that liquid is blocked from entering that portion of the second lumen distal to the port and from entering the first lumen through the aperture in the septum. Such a sealant plug may either be formed in situ or may be pre-formed and secured in place through the lateral port in the catheter body.

Other objects and advantages of the invention will be apparent from the specification and drawings.

DRAWINGS

FIG. 3 is an enlarged broken longitudinal sectional view of the distal portion of the catheter.

FIG. 4 is a cross sectional view taken along line 4—4 of FIG. 3.

FIG. 5 is an enlarged cross sectional view taken along line 5—5 of FIG. 3.

FIG. 6 is an enlarged cross sectional view taken along line 6—6 of FIG. 3.

FIGS. 7 and 8 are somewhat schematic views illustrating a sequence of steps in performing the method of this invention.

DETAILED DESCRIPTION

Figure 1:
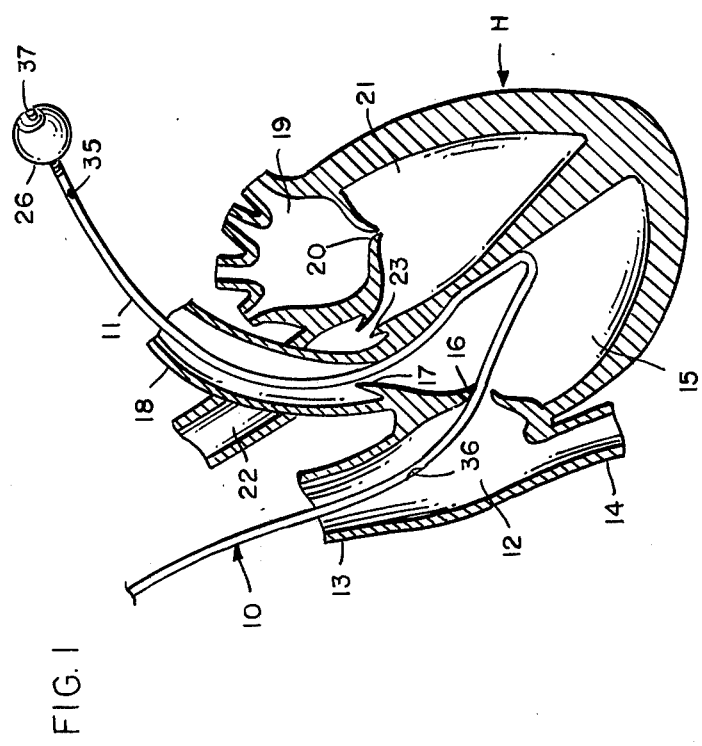
FIG. 1 is a somewhat diagramatic sectional view illustrating a flow-directed catheter of this invention when such a catheter is positioned for use.

FIG. 1 illustrates a catheter 10 extending to the right side of a patient's heart H. In brief, the parts of the heart and their operation are as follows: the right atrium 12 receives blood from the superior and inferior vena cava veins 13 and 14 and pumps such blood into the right ventricle 15 through the tricuspid valve 16. From the right ventricle, the blood travels to the lungs through pulmonary valve 17 and pulmonary artery 18. Oxygenated blood returning from the lungs enters left atrium 19 and then passes through mitral valve 20 into right ventricle 21. The blood leaves the heart through aorta 22 after passing through aortic valve 23.

Catheter 10 is depicted as a multi-purpose flow-directed catheter having a tubular body 11 equipped at its distal end with pressure responsive means in the form of a balloon 26. At its proximal end, the catheter body terminates in a coupling 27 which operatively connects the lumens of the catheter to connector tubes 28, 29, and 30. Connector tube 29 bifurcates to provide branches 29a and 29b and, as well known in the art, all of the tubes or branches are provided with coupling elements 31-34 for attaching the connector tubes to syringes or other devices.

The structure as so far described is essentially conventional. In use, the soft, pliable catheter body is introduced into the vascular system from the antecubital, femoral, subclavian, or jugular areas and is advanced, with the balloon in deflated or only partially inflated condition, into the right atrium 12. The balloon is then inflated to its maximum recommended capacity and the flow of blood through the heart rapidly propels the inflated balloon-tipped catheter from the right atrium into the pulmonary artery 18 (FIG. 1). It will be observed that when the catheter is so positioned, balloon 26 has advanced through the pulmonary artery into what is generally referred to as the pulmonary capillary wedge position, a sensor or other electrical element 35 at the distal end portion of the catheter body (just proximal to the balloon 26) is disposed within the pulmonary artery, and a lateral flow port 36, sometimes referred to as a proximal port (in contradistinction to distal port 37 at the tip of the catheter body distal to the balloon) is positioned within right atrium 12. With the catheter so positioned, a variety of diagnostic procedures may take place, all of which are well known and, therefore, will be described only briefly here. Port 36 may be used for taking pressure measurements from the right atrium, for injecting or infusing solutions, or for taking blood samples, whereas distal port 37 may also be used for sampling, infusion or injection, or measuring pulmonary artery and pulmonary capillary wedge pressures (depending on whether such measurements are taken with balloon 26 inflated or deflated). In thermodilution measurements, a sterile, cold solution is injected into the right atrium through port 36 and the resulting change in blood temperature is detected by thermistor 35, thereby allowing calculation of cardiac output.

It is to be understood that the electrical element 35 need not be in the form of a thermistor; it may, for example, be an electrode for sensing (or, if necessary, stimulating) electrical activity of the heart as disclosed in detail in co-owned U.S. Pat. No. 3,995,623. However, unlike the construction disclosed in that patent, which has four lumens extending through the catheter body, the catheter of the present invention is capable of performing the same functions with only three lumens.

As shown in FIG. 4, catheter body 11 is divided by a three-branched partition or septum 40 so that it defines three parallel lumens 41, 42, and 43. Lumen 41 is a through lumem which communicates with connector tube 28 and which extends all of the way to distal port 37. Such a lumen is illustrated because of the functions already described with which such distal port is associated; if such functions are regarded as unnecessary, then it is to be understood that through lumen 41 may be eliminated and the sapce that would otherwise be occupied by that lumen may be used for increasing the size of lumens 42 and 43, or for providing a lumen intended to perform some other purpose, or for reducing the outside cross sectional dimensions of the catheter body.

Lumen 42 is a passage which communicates with connector tube 29 and which contains electrical leads 44 extending to the electrical element 35 located within the lumen near balloon 26. As shown most clearly in FIG. 3, the element 35, which takes the form of a thermistor, is embedded in a suitable embedding medium 46 adjacent an opening 47 formed in the outer wall of the catheter body. Any appropriate embedding medium may be used.

Figure 2:
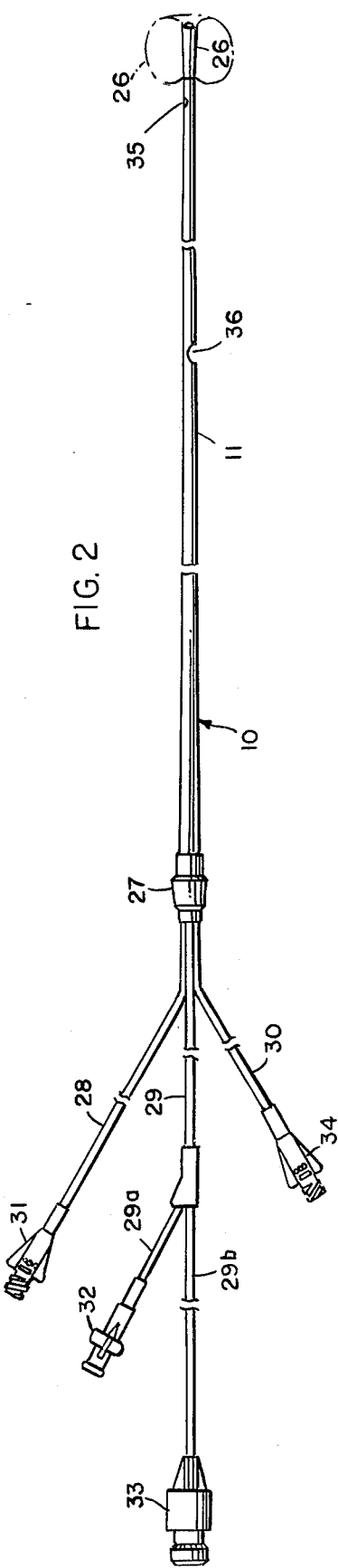
FIG. 2 is a side elevational view of the catheter.

Lumen 43 is the lumen which carries liquids to or from proximal port 36. As indicated, that port is so named because it is a substantial distance from the tip of the catheter and from distal port 37; however, as shown in FIG. 2, port 36 is actually located in an intermediate position. Thus, in a typical catheter having a total body length of approximately 110 centimeters, the distance between the proximal lumen and the distal tip would ordinarily fall within the rnge of approximately 15 to 35 centimeters, such distance being selected so that, when the catheter is positioned as shown in FIG. 1, port 36 will be disposed in the right atrium or superior vena cava.

At its proximal end, lumen 43 communicates with connector tube 30 and coupling 34. As already stated, lumen 42 communicates with connector tube 29. Leads 44 extend from that lumen into connector tube 29, branch 29b, and coupling 33. As is well known, coupling 33 may be connected to a thermodilution cardiac output computer or, should electrical element 35 take the form of an electrode rather than a thermistor, to other appropriate electronic equipment.

Portions of both lumens 42 and 43 are used to define the flow passage for gas for inflating and deflating balloon 26. The gas of choice is carbon dioxide because of its relatively rapid diffusion rate in blood should the balloon rupture; however, it is conceivable that other gases might be used or even recommended under special circumstances. Furthermore, while a balloon is represented in the drawings and described in detail herein for purposes of illustration, other types of pressure responsive means might be substituted. For example, the pressure responsive means might take the form of a diaphragm-equipped pressure transducer for measuring blood pressure at or near the tip of the catheter, the trans-luminal gas pathway in such a case serving to vent the inside surface of the diaphragm to atmosphere.

Where the pressure responsive element 26 comprises a balloon as shown, the gas enters and leaves the balloon chamber through a lateral port 48 formed in the wall of catheter body 11 (FIG. 3). The balloon 26 may be secured in place in any suitable manner, reference being made to U.S. Pat. Nos. 3,995,623, 3,746,003, and 3,833,004 for further information in that regard. Since balloon-attachment methods and constructions are well known in the art and and form no part of the present invention, a more detailed description is believed unnecessary herein. It should be noted, however, that the balloon is shown in its fully deflated condition in FIG. 3 and FIG. 2 (solid lines) and in fully inflated condition in FIG. 1 and in FIG. 2 (phantom lines).

Septum 40 is provided with an aperture 49 that places lumens 42 and 43 in flow communication. In the embodiment depicted in FIG. 3 that aperture 49 is located in close proximity to port 36; more specifically, just distal to the port. A sealant plug 50 is located lumen 43 between port 36 and aperture 49 and performs the multiple functions of sealing the distal portion of lumen 43 against the ingress of liquid, blocking the flow of liquid on the proximal side of the plug from entering lumen 42 through aperture 49, and maintaining the distal portion of lumen 43 (i.e., the portion distal to port 36) in open communication with that portion of lumen 42 proximal to element 35. If the catheter body is formed of polyvinyl chloride, than a sealant plug material composed of has been found effective; however, it is to be understood that any of a variety of materials may be selected for the catheter body and for the sealant plug.

From the foregoing, it is believed apparent that the catheter of the present invention requires one less lumen than prior catheters to achieve the same monitoring or diagnosing functions, and that the elimination of one lumen permits size adjustments which result in either improved performance characteristics, or smaller external size, or both. For example, it has been found that a three-lumen catheter of the present invention of 4 French size has performance characteristics (flow capacity and frequency response) approximating those of a substantially larger (outside diameter) prior art four-lumen catheter of size 6 French.

The wires or leads 44 for electrical element 35 are insulated although such insulation is intended primarily to prevent the conductors for making electrical contact with each other since the sealant plug 50 effectively prevents liquid from invading lumen 42 through port 36 or from the proximal portion of lumen 43. The leads are also protected against contact with blood flowing into lumen 42 should balloon 26 rupture in use because blood entering lumen 43 in the vicinity of the balloon would clot and seal lumen 43 long before reaching aperture 49.

Certain steps of fabricating the catheter are illustrated in FIGS. 7 and 8. After the proximal port 36 has been formed in the catheter body at a point intermediate its length, an aperture-forming tool 55 is inserted through the port and into contact with septum 40 (FIG. 7). In the method shown, the tool is inserted at a forwardly-directed angle in order to form aperture 49 at a point distal to port 36. The tool or probe may be heated to cause the thermoplastic material of septum 40 to melt upon contact and thereby develop aperture 49, although it is believed apparent that other cutting or piercing techniques may be used to form that aperture.

After aperture 49 has been formed, sealant may be injected from a nozzle 56 into lumen 43, again using port 36 as an access opening (FIG. 8). Upon solidification, the sealant forms plug 50 which seals the distal portion of lumen 43 from any liquid invasion from port 36 or the proximal portion of lumen 43 and, at the same time, maintains the distal portion of lumen 43 in direct communication with lumen 42 through aperture 49. Preferably, the trailing surface of plug 50 is contoured as shown in FIG. 3 to help direct the flow of liquid exiting port 36 (and discharged from a syringe connected to coupling 34 and connecter tube 30) or entering that port for the taking of samples or pressure measurements. In the case of pressure measurements, it is to be understood that couplings 41 and/or 34 would be connected to any of a variety of pressure measuring devices rather than to syringes.

Figure 9:
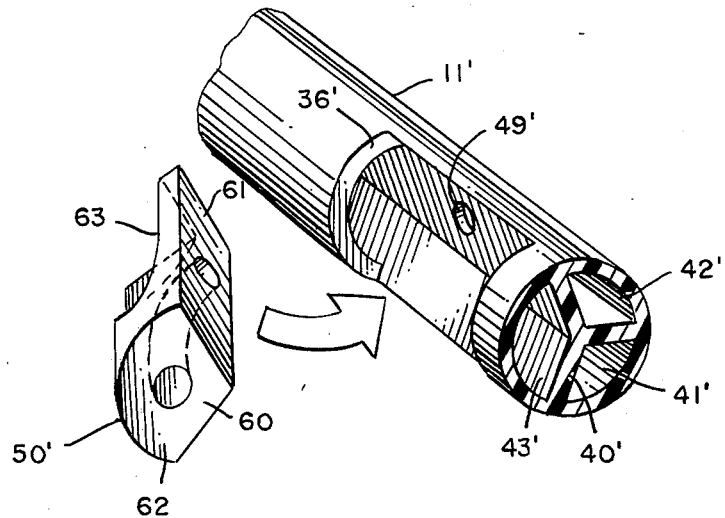
FIG. 9 is a fragmentary exploded perspective view illustrating a second embodiment of this invention, such view depicting a pre-formed sealant plug as it is being moved into position within the catheter body.
Figure 10:
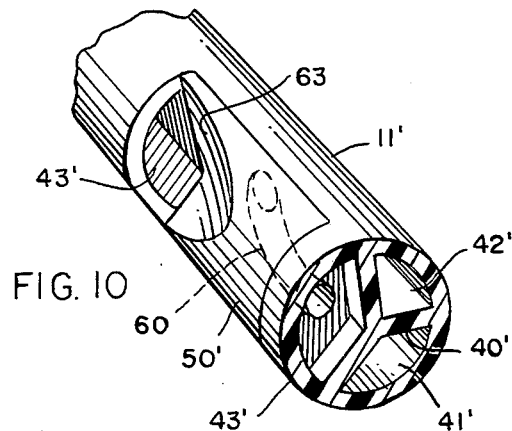
FIG. 10 is a fragmentary perspective view of the embodiment of FIG. 9 showing the sealant plug in fully inserted position.

While the method disclosed herein necessarily involves the use of port 36 as an access opening for the formation of aperture 49, it is not essential that the aperture be formed on the distal side of the port, especially if the sealant plug is pre-formed as indicated in FIGS. 9 and 10. In FIG. 9, it will be seen that sealant plug 50' is pre-formed to fit within port or opening 36' in the wall of catheter body 11'. Aperture 49', which may be substantially smaller than port 36' (since the aperture is required only to transmit gas for balloon inflation and deflation), may be located within the axial limits of port 36'.

The pre-formed plug 50' is dimensioned to fit within the area of lumen 43' outlined by opening 36' and, when sealed in place by a suitable solvent, cement, or other suitable means, appears as shown in FIG. 10. The plug is formed with two passages, one passage 60 extending from face 61 to the distal end 62 and being aligned with aperture 49' when the parts are assembled for the purpose of placing that aperture (and lumen 42') in communication with the portion of lumen 43' distal to the plug. The second passage or recess 63 simply contributes in defining the flow port and, as shown most clearly in FIG. 10, helps to direct liquid into or out of the proximal portion of lumen 43' without allowing such liquid to enter other lumens or any portions of the catheter distal to the plug.

While in the foregoing I have disclosed embodiments of the invention in considerable detail for purposes of illustration, it will be understood by those skilled in the art that many of these details may be varied without departing from the spirit and scope of the invention.

I claim:

1. A catheter comprising a catheter body having an elongated tubular wall formed of flexible material and having proximal and distal ends; pressure responsive means mounted upon said body adjacent the distal end thereof; said catheter body having first and second lumens extending from said proximal end to said distal end and separated by a longitudinal septum; a port in said wall of said body communicating with said second lumen and being located intermediate said distal and proximal ends; at least one electrical lead extending through portions of said first lumen both proximal and distal to said port; sealant plug means disposed within said second lumen adjacent said port to block communication between the portion of said second lumen proximal to said port and the portion of said second lumen distal to said port without obstructing flow communication between said proximal portion of said second lumen and said port; and an aperture through said septum to place said distal portion of said second lumen in communication with said first lumen.

2. The catheter of claim 1 in which said aperture is smaller than said port.

3. The catheter of claim 1 in which said aperture is located in said septum on the distal side of said port.

4. The catheter of claim 3 in which said sealant plug means is disposed within said second lumen between said port and said aperture, thereby blocking flow communication between said first lumen and the proximal portion of said second lumen without obstructing communication either between said proximal portion of said first lumen and said distal portion of said second lumen or between said proximal portion of said second lumen and said port.

5. The catheter of claim 1 in which said aperture is disposed in said septum adjacent to said port.

6. The catheter of claim 5 in which said aperture is located in said septum within the axial limits of said port.

7. The catheter of claim 6 in which said sealant plug means comprises a pre-formed plug permanently sealed in place within said port; said plug having a first passage extending between and communicating with said aperture and said distal portion of said second lumen, and a second passage communicating with the proximal portion of said second lumen and the exterior of said plug.

8. The catheter of claims 1, 2, 3, 4, 5, 6 or 7 in which said pressure responsive means comprises an inflatable balloon and said first lumen communicates with said balloon through an opening in said wall of said body.

9. A method of forming a gas flow passage in a catheter having proximal and distal ends and having a plurality of parallel lumens therein, a first one of said lumens being adapted to receive at least one electrical lead therein and being separated from a second lumen adapted for conducting liquids; comprising the steps of forming a lateral port in the outer wall of said body at a point intermediate the length thereof, said port communicating only with said second lumen and constituting an opening for the inflow and outflow of liquids with respect thereto; introducing a tool through said port to form an aperture in said septum placing said first and second lumens in communication with each other; then introducing a sealant plug into said second lumen through said port to (a) block communication between the portion of said second lumen proximal to said port and both said aperture and the portion of said second lumen dista to said port, and (b) maintain said distal portion of said second lumen in open communication with said first lumen through said aperture and said proximal portion of said second lumen in open communication with said port, whereby said proximal portion of said first lumen and said distal portion of said second lumen may be utilized together to define a gas flow pathway.

10. The method of claim 9 in which the aperture formed in said septum is smaller than said port.

11. The method of claim 9 in which said aperture is formed within said septum within the axial limits of said port, said sealant plug being inserted in pre-formed condition through said port and into said second lumen and being permanently secured therein.

12. The method of claim 9 in which said aperture is formed in said septum on the distal side of said port, said sealant plug being introduced and secured within said second lumen between said port and said aperture.

13. The method of claim 12 in which said sealant plug is formed of a flowable material capable of passing into a hardened state and is introduced into said second lumen in flowable form.

14. A method of forming a gas flow passage in a catheter having proximal and distal ends and having a plurality of parallel lumens therein, a first one of said lumens being adapted to receive at least one electrical lead therein and being separated from a second lumen adapted for conducting liquids; comprising the steps of forming a lateral opening in the outer wall of said body communicating only with said second lumen; introducing a tool through said opening to form an aperture in said septum placing said first and second lumens in communication with each other; then introducing a sealant plug into said second lumen through said opening to form a trans-luminal flow passage between the portion of said first lumen proximal to said opening and a portion of said second lumen distal to that opening.

15. The method of claim 14 in which said aperture is formed within said septum within the axial limits of said opening, said sealant plug being inserted in pre-formed condition through said opening and into said second lumen and being permanently secured therein.

16. The method of claim 14 in which said sealant plug is formed of a flowable material capable of passing into a hardened state and is introduced into said second lumen in a flowable form.

* * * * *